United States Patent [19]

Prestele

[11] 4,197,859
[45] Apr. 15, 1980

[54] APPARATUS FOR THE DETERMINATION OF THE RESPIRATORY PASSAGEWAY IMPEDANCE

[75] Inventor: Karl Prestele, Erlangen, Fed. Rep. of Germany

[73] Assignee: Siemens Aktiengesellschaft, Berlin & Munich, Fed. Rep. of Germany

[21] Appl. No.: 886,724

[22] Filed: Mar. 15, 1978

[30] Foreign Application Priority Data

Mar. 30, 1977 [DE] Fed. Rep. of Germany ....... 2714216

[51] Int. Cl.² ............................................. A61B 5/08
[52] U.S. Cl. .................................................. 128/720
[58] Field of Search ............. 128/2.08, 2.07, DIG. 29, 128/719, 720, 716

[56] References Cited

U.S. PATENT DOCUMENTS

| | | | |
|---|---|---|---|
| 3,598,111 | 8/1971 | Kahn et al. | 128/2.08 |
| 3,713,436 | 1/1973 | Hardway, Jr. | 128/2.08 |
| 3,726,271 | 4/1973 | Mondshine et al. | 128/2.08 |
| 4,051,843 | 10/1977 | Franetzki et al. | 128/2.08 |
| 4,082,088 | 4/1978 | Franetzki et al. | 128/2.08 |
| 4,127,115 | 11/1978 | Franetzki | 128/2.08 |

OTHER PUBLICATIONS

Ross et al., "Direct Readout of Respiratory Impedance", Med. & Biol. Eng., vol. 14, No. 5, pp. 558–564, Sep. 1976.

Primary Examiner—Lee S. Cohen
Attorney, Agent, or Firm—Hill, Van Santen, Steadman, Chiara & Simpson

[57] ABSTRACT

In the illustrated embodiment, applied high frequency flow is divided into a first flow component traversing a known flow impedance and a second flow component directed toward the mouthpiece of a breathing tube. During calibration, the mouthpiece is sealed, and phase adjustments are made such that during measurement, applied flow and first flow component representing signals are essentially in phase and can be combined in an a.c. subtracter to provide a measure of the second flow component. A divider provides the quotient of rectified average pressure and second flow component signals as a measure of the magnitude (Z) of respiratory passageway impedance. A phase difference measurement circuit measures the phase difference between pressure and second flow components and can be switched over during calibration for use in the phase adjustment procedure. The real and imaginary components of respiratory passage impedance can be obtained using sample and hold circuitry responsive to the phase of the second flow component.

16 Claims, 4 Drawing Figures

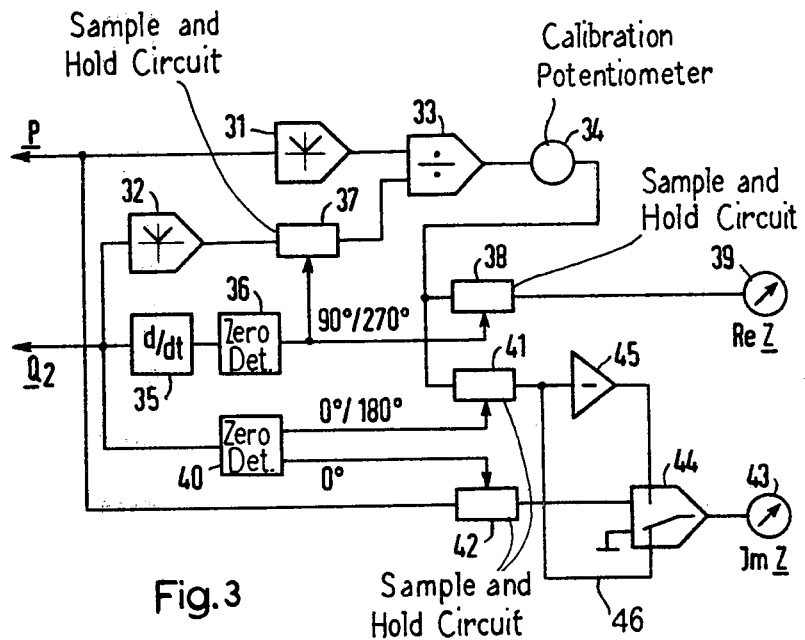
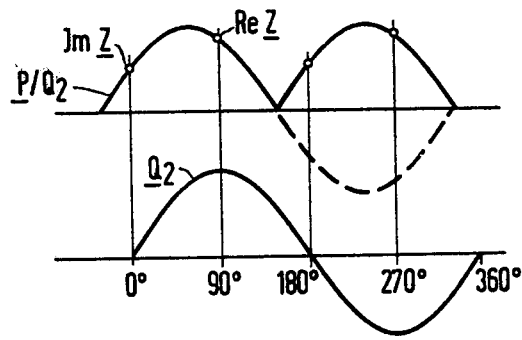
Fig. 3
Fig. 3A

APPARATUS FOR THE DETERMINATION OF THE RESPIRATORY PASSAGEWAY IMPEDANCE

BACKGROUND OF THE INVENTION

The invention relates to an apparatus for determining the respiratory passageway impedance comprising a breathing tube which exhibits a pulse generator for subjecting the breath flow with flow pulsations of a higher frequency as compared with the respiratory frequency, and which exhibits a selective pressure measuring apparatus for the correspondingly higher-frequency pressure fluctuations, and whose tube-end not facing the mouthpiece is terminated with a flow resistance having a known resistance value; for example, a hose, as the comparison resistance, such that a first partial current of the higher frequency total current flows over the flow resistance, whereas a second partial current flows via the mouthpiece into the respiratory tract of an examination subject.

An apparatus of the type initially cited is known from the U.S. Pat. No. 4,051,843. With an apparatus of this type, the respiratory passageway resistance can be indicated rapidly and in a problem-free manner as a function of the impressed flow, the complex comparison flow impedance having a known impedance value, and the measured pressure valve. In a further development of an apparatus of this type, means were provided in the measuring apparatus for the simultaneous detection of the phase angle of the pressure measured value and means for representing, or converting, respectively, the measured value with the object of determining the magnitude and phase of the complex respiratory passageway impedance. However, the equations derived for this purpose show that the connection between the measured values and the magnitudes to be determined is relatively complicated. In said letters patent, the complex respiratory passageway impedance must first be determined from diagrams with curved coordinates, or by means of programmable computers, respectively.

SUMMARY OF THE INVENTION

It is an object of the invention to further develop an apparatus of the type initially cited such that the respiratory passageway impedance can be indicated (or displayed) directly ("on line") and in linear fashion according to magnitude and phase, or that it can also be indicated as a real and an imaginary component. The cumbersome evaluation of diagrams and the programming of computers, respectively, is to be entirely eliminated here.

In accordance with the invention, the object is achieved by virtue of the fact that, in order to determine that particular second partial current of the superimposed higher-frequency total current which flows via the mouthpiece into the respiratory tract of the subject under examination, the first partial current which flows via the comparison impedance and whose magnitude is established by the quotient of the higher frequency pressure signal and the known comparison impedance, is subtracted by means of a subtracter element from the likewise known total current, whereby, in order to determine the magnitude and phase, or the real (and imaginary) component of the respiratory passageway impedance, a phase tuning device is series connected specifically to the subtracter element, said phase tuning device bringing the total current and the first partial current into phase in a calibration operation while the breathing tube is sealed (or closed) off at the mouthpiece. In order to determine the phase of the respiratory passageway impedance, a phase measuring device with a calibrated indicator apparatus is connected in the signal path for the second partial current behind the subtracter element, on the one hand, and in the pressure signal path in front of the phase tuning device, on the other hand, whereby, in the calibration operation, carried out with the breathing tube closed (or sealed) off at the mouthpiece, the phase measuring device connected to the signal path for the total current and the first partial current is calibrated to zero (or null) value by means of the phase tuning device. Thus, with the apparatus according to the invention, an "on line" display (or indication) of the magnitude and phase, or the real- and imaginary-component of the respiratory passageway impedance, is achieved. The technical outlay involved remains within reasonable limits.

A detailed analysis of the pneumatic conditions in the known apparatus for determining the respiratory passageway impedance (according to FIG. 1) served as the basis of the invention. From the parallel-connection of the respiratory passageway impedance Z and the comparison impedance $Z_o$, in analogy with laws of electrical engineering, there result the equations for the currents $Q_i$ and the impedances $Z_i$:

$$Q_1 + Q_2 = Q_o = \text{Const.} \quad (1)$$

$$\frac{1}{Z_o} + \frac{1}{Z} = \frac{Q_o}{P} \quad (2)$$

The symbols here denote the following (complex) magnitudes:

| | |
|---|---|
| $\underline{Z} = Z \cdot e^{j\phi}$ | (Respiratory passageway impedance) |
| $\underline{Z}_o = Z_o \cdot e^{j\phi_o}$ | (Comparison impedance) |
| $\underline{Q}_o = Q_o \cdot e^{j\omega t}$ | (impressed pulsation) |
| $\underline{Q}_1 = Q_1 \cdot e^{j(\omega t + \phi_1)}$ | (first partial current flowing over the comparison impedance) |
| $\underline{Q}_2 = Q_2 \cdot e^{j(\omega t + \phi_2)}$ | (second partial current flowing over the respiratory passageway impedance of the test subject) |
| $\underline{P} = P \cdot e^{j(\omega t + \psi)}$ | (mouth pressure) |

If equation (2) is solved according to Z, the respiratory passageway impedance is basically determinable as a function of the specified (or predetermined), and measurable magnitudes. In the case of known apparatus, the second partial current $Q_2$ is particularly also measured with a pneumotachograph in the respiratory current passageway, whereby, as a consequence, however, due to the unavoidable errors during the measurement of small alternating currents of high frequency, the value, according to magnitude and phase, of the respiratory passageway resistance becomes imprecise.

However, in accordance with the present invention, $Q_2$ is electronically determined. The circuit proceeds from the definition-equation for a flow impedance as a quotient of alternating pressure and alternating current; specifically for the magnitude and phase of the respiratory passageway impedance in an apparatus of the type initially cited the following relations are then valid:

$Z = P/Q_2$ and $\phi = \psi - \phi_2$ with $Q_2 = Q_o - Q_1$ and $Q_1 = P/Z_o$, $\phi_1 = \psi - \phi_o$ If the second partial current $Q_2$ is known according to magnitude and phase, then the magnitude of the respiratory passageway impedance Z can be determined by means of quotient formation in a divider member, and the phase of the respiratory passageway impedance can be determined by means of direct phase measurement. For the real- and imaginary-component of the respiratory passageway impedance Z, as is known, the following relations are valid:

$$Re(Z) = Z \cos \phi$$

$$Im(Z) = Z \sin \phi$$

However, the invention preferably proceeds from the fact that the pressure divided by the magnitude of the second partial current, at the time of maximum flow corresponds to the real component, and that this quotient corresponds to the imaginary component of the respiratory passageway impedance during zero (or null) instantaneous value of the flow. In an advantageous further development, the corresponding voltages are retained (or held) with sample- and hold-elements, whereby the sample pulses are supplied by means of extreme or peak value detectors- or zero (or null) value detectors, respectively, in the signal line for the second partial current.

Further advantages and details of the invention shall be apparent from the following description of a sample embodiment on the basis of the accompanying sheets of drawings; other objects, features and advantages will be apparent from this detailed disclosure and from the appended claims.

BRIEF DESCRIPTION OF THE DRAWINGS

FIG. 3 illustrates a block circuit diagram according to the invention for determining the real component and the imaginary component of the respiratory passageway impedance; and FIG. 3A is a waveform diagram useful for explaining the operation of the embodiment of FIG. 3.

DETAILED DESCRIPTION

Figure 1:
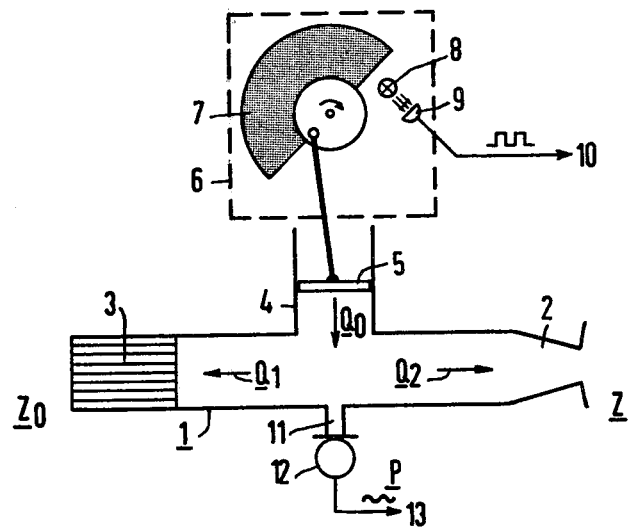
FIG. 1 schematically illustrates the pneumatic portion of the apparatus for determining the respiratory passageway resistance which is similar to the apparatus known from the U.S. Pat. No. 4,051,843.

In FIG. 1, 1 designates a breathing tube, at the one end of which a mouthpiece 2 is located for the purpose of connecting the test subject, whose respiratory tract is represented by the complex respiratory passageway impedance Z. At the other end of the breathing tube leading into free space, there is arranged a complex comparison impedance 3 with the value $Z_o$. There is disposed on the breathing tube 1 a connecting branch 4 for the purpose of connecting an alternating flow pump 5 with an impressed, known flow pulsation $Q_o$, whose frequency lies above the breathing frequency. In accordance with the rule of sums, the total current $Q_o$ branches at the juncture of connecting branch 4 with tube 1 into the two partial currents $Q_1$ and $Q_2$. The schematically illustrated alternating flow pump 5 is connected to a drive unit 6. There is mounted onto the drive unit 6 a semicircular plate (or disk) 7 which, when drive unit 6 is in operation, periodically interrupts the path of rays of a light barrier constructed from an optical transmitter 8 and optical receiver 9. A square wave signal for $Q_o$ is thereby produced synchronously with the operation of the alternating flow pump 5, said signal being conveyed via signal line 10 to the evaluation unit. In addition, there is disposed on breathing tube 1 a tapping (or measuring) connection piece 11 for measuring pressure. Via a microphone 12 operating as a sensing transducer, pressure signal P is likewise conveyed in the form of an electrical signal via signal line 13 to the evaluation unit.

Figure 2:
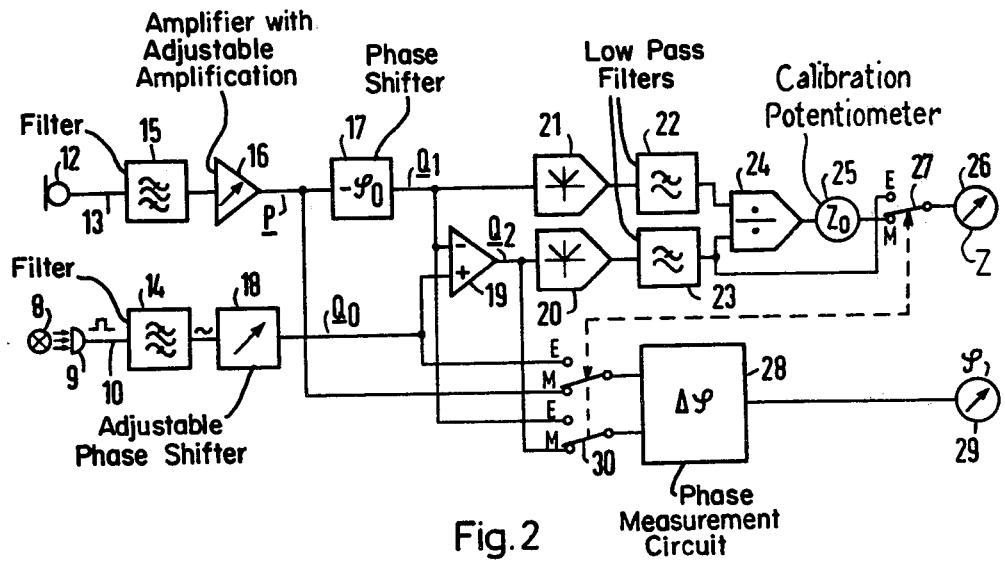
FIG. 2 illustrates a block circuit diagram according to the invention for determining the magnitude and phase of the respiratory passageway impedance.

In FIG. 2, light barrier 8, 9 with signal line 10, as well as pressure transducer 12 with signal line 13 from FIG. 1 is schematically illustrated. The square wave signal of light barrier 8, 9, is first delivered to a selective filter 14 for the alternating frequency, which filters out (transmits) the fundamental wave of the square wave signal; i.e., a continuous sinusoidal waveform signal as the fundamental wave, said fundamental sine wave signal being synchronous with the alternating flow pump 5. A phase-synchronous signal for $Q_o$ is thus available. Instead of light barrier 8, 9, it is also possible to employ as the signal generator a permanent magnet rotating with the pump drive 6, said permanent magnet inducing in a fixed coil an alternating current synchronous with the impressed alternating flow $Q_o$. The output signal of measuring transducer 12 is likewise initially conveyed via line 13 to a filter 15 which is selective for the alternating frequency, which separates (transmits) the higher frequency pressure component corresponding in frequency to the flow pulsation $Q_o$ from the respiratory pressure component. Via an amplifier 16 with adjustable amplification, the pressure signal is conveyed to a phase shifter 17 with which the known phase angle $\phi_o$ of the comparison impedance $Z_o$ is compensated. In the case of a real comparison impedance ($\phi_o = 0$), the phase shifter 17 can be eliminated. Thus, the output signal of the phase shifter member 17 represents a signal which is phase-synchronous with the first partial current $Q_1$. The fundamental sine wave output signal, which is phase-synchronous with $Q_o$, of filter 14 is delivered via an adjustable phase shifter 18, together with the output signal—which is phase synchronous with $Q_1$—of phase shifter 17 to a subtracter unit 19. With the adjustable phase shifter member 18, the phase relationship between $Q_o$ and $Q_1$ is initially equalized (or balanced) in the calibration operation while the breathing tube 1 is closed (or sealed) off at the mouthpiece 2. During the measurement operation, the difference between $Q_o$ and $Q_1$ is then formed by means of subtracter unit 19, whereby a phase-synchronous signal for $Q_2$ results. In order to determine the magnitude Z of the respiratory passageway impedance Z, the output signals of the phase shifter 17 and the subtracter unit 19 are then delivered, for the purpose of full wave rectification in each instance, to amplitude members 20 and 21 with following low-pass filters 22 and 23, for the purpose of mean value formation of the rectified signals, and subsequently the quotient of the averaged magnitudes is determined in a divider element 24. The output signal of output divider element 24 still merely needs to be weighted (or evaluated) in a calibration potentiometer 25 with the factor $Z_o$, and it can then be directly indicated on a calibratable indicator 26 as the magnitude of the respiratory passageway resistance Z. The indicator apparatus 26 can be switched over by means of switch 27 from a measurement position M to a calibration position E. In the calibration position E, the absolute value of $Q_2$ is delivered directly to display apparatus 26.

In order to determine the phase angle $\phi$ of the respiratory passageway impedance Z, the sinusoidal output signals of amplifier 16 and subtracter unit 19 (i.e., the signal lines for P and $Q_2$) are delivered to measurement inputs M of a phase measurement element 28 with a following indicator unit 29 which determines the phase difference of the input signals in a conventional manner. The phase measurement element 28 additionally has two calibration inputs E to which the signal lines carrying $Q_1$ and $Q_o$ can be connected for the purpose of calibration. A switch 30 is here coupled in front of the phase measurement element 28 with switch 27 such that both indicator units 26 and 29 can each be simultaneously brought into calibration position.

For zero (or null) balance of the circuit according to FIG. 2, the breathing tube according to FIG. 1 is tightly closed (or sealed) off at the mouthpiece 2, and switches 27 and 30, respectively, are set to the calibration position E. Since, on account of $Z \to \infty$, the relations $Q_2=0$, and $Q_1=Q_o$ are pneumatically valid, the signals for $Q_1$ and $Q_o$ must be made identical in phase and amplitude in the calibration position. Accordingly, with phase shifter unit 18, the phase of $Q_o$ is adjusted such that the value of zero is indicated on indicator apparatus 29. The amplitude of $Q_1$ is then adjusted at the adjustable amplifier 16 such that a minimum value is present on the indicator apparatus 26. The limit indication of zero (or null) can be only achieved if the signals for $Q_o$ and $Q_1$ are completely free of harmonic components. Subsequent to the zero (or null) balance, in the measurement position M of switch 27, with the aid of a known calibration resistance which is connected to the mouthpiece 2 according to FIG. 1 instead of the test subject, the amplitude deflection of the indicator apparatus 26 is adjusted to a calibration mark by means of potentiometer 25. The indicator apparatus 26 is thus calibrated for the measurements.

The circuit in FIG. 3 proceeds from the circuit means illustrated in FIG. 2 for determining the second partial current $Q_2$ (at the output of subtracter 19) and the pressure signal value P (at the output of adjustable amplifier 16). In order to directly detect the real component and the imaginary component of the respiratory passageway impedance, the quotient $P/Q_2$ is retained (held) at specific times in each instance. The circuit is based on the fact that the pressure value P, divided by the magnitude of $Q_2$ corresponds at the time of the maximum and the minimum (i.e. at the time of the peak positive and peak negative instantaneous values) of the second partial current $Q_2$ (i.e. $\phi_2=90°$, 270°) to the real component, and that at the time of zero (or null) instantaneous values of the second partial current $Q_2$ (i.e. $\phi_2=0°$, 180°), it corresponds to the imaginary component of the respiratory passageway impedance Z. The corresponding voltages in the signal lines are retained or held with sample- and hold-elements. The sample pulses are obtained with zero (or null) value detectors. Prior to the quotient formation, the P- and $Q_2$ signal again undergo a full-wave rectification at amplitude elements 31 and 32. There are supplied to the divider element 33 and the following calibration potentiometer 34 (analogously to FIG. 2) the rectified pressure signal and the magnitude signal of the second partial current $Q_2$.

In the time diagram, the resistance signal $P/Q_2$ is illustrated together with the phase shifted $Q_2$ signal. From this illustration, it is apparent that during the zero (or null) instantaneous value of the second partial current, the measured value represents the pure imaginary component, and during maximum or minimum values of the second partial current, on the contrary, the measured value represents the pure real component of the respiratory passageway impedance Z. Accordingly, the circuit according to FIG. 3 exhibits a differentiating element 35 with a following zero (or null) detector 36, to which the second partial current $Q_2$ is delivered, so that, by means of zero (or null) detector 36, sample pulses are supplied in the time intervals $\phi_2=90°$, or 270°, respectively. The output signal of zero detector 36, on the one hand, actuates a sample and hold circuit 37 (for the purpose of peak value formation of $Q_2$. Circuit 37 has its input connected to rectifier 32 and its output connected to divider element 33. The output signal from zero detector 36, on the other hand, is supplied to an additional sample and hold circuit 38, which is connected with the output of divider element 33 via a calibration potentiometer 34. Thus, with this interconnection, the value of $P/Q_2$ is determined at the times $\phi_2=90°$, 270°, which represents the real component of the respiratory passageway impedance Z, and which is indicated as the measured value on the display apparatus 39.

There is further connected to the input $Q_2$ of FIG. 3 a zero detector 40 for detecting the zero crossings of the second partial current $Q_2$. The zero detector 40 has two outputs, the first output of which delivering sample pulses in the times $\phi_2=0°$, 180° to a sample and hold element 41 in the output line for the quotient $P/Q_2$, and the second output of which, on the contrary, merely delivering a pulse at the times corresponding to $\phi_2=0°$, which actuates a sample and hold element 42 in the pressure signal line. The output signal of the sample and hold element 41 represents the magnitude of the imaginary component of the respiratory passageway impedance Z. However, since the imaginary component can be positive or negative; i.e., it can be of an inductive or of a capacitive nature, a polarity determination must take place before the ascertained value is indicated as the measured value on an indicator apparatus 43. The imaginary component of the respiratory passageway impedance Z is positive or negative, respectively, when the pressure signal P at the time $\phi_2=0°$ is greater, or smaller, respectively, than zero. The pressure signal P is retained (or held) at this time interval by means of the sample and hold element 42, whose output signal proceeds to the first input of a comparator 44. The second input of comparator 44 is connected to ground potential. In the case of a positive output voltage of sample and hold element 42, the indicator instrument 43 is connected directly via line 46 and the comparator 44 to the output of the sample and hold element 41. If, on the contrary, the output signal is negative, the display apparatus 43 is connected by means of comparator 44 to the output of an inverter 45, which is connected to the output of the sample and hold element 41. An indication, which is true to the polarity of the imaginary component of the respiratory passageway impedance Z is thereby guaranteed on the indicator apparatus 43.

As will be apparent the zero detector 40 may include a zero crossing detector circuit for the full sine waveform shown in the lower part of FIG. 3A for providing actuating pulses for circuit 41 at the zero crossings of the lower waveform of FIG. 3A. To transmit pulses for zero crossings only at phase angle 0° and not at 180° for actuation of circuit 42, a differentiator circuit of component 40 may generate a positive pulse at 0° and a negative pulse at 180° from the waveform at the lower part of FIG. 3A, and a diode may transmit only the positive pulses from the differentiator; and such transmitted positive pulses then may be used to gate out only the zero crossing pulses at phase 0° to circuit 42.

It will be apparent that many modifications and variations will be effected without departing from the scope of the novel concepts and teachings of the present invention.

I claim as my invention:

1. Apparatus for the determination of the respiratory passageway impedance, said apparatus comprising a breathing tube having a mouthpiece at one end, having a pulse generator means (5, 6) coupled with said breathing tube for producing an impressed higher frequency total current ($Q_o$) of a higher frequency as compared with the respiratory frequency, thereby to subject the breath flow with flow pulsations of a higher frequency as compared with the respiratory frequency, and having a selected pressure measuring means (12) coupled with said breathing tube for responding to the correspondingly higher frequency pressure fluctuations for providing a pressure signal (P) of the higher frequency, the end of the breathing tube remote from the mouthpiece having a flow impedance (3) with a known impedance value ($Z_o$) for serving as a comparison impedance, such that a first partial current ($Q_1$) of the higher frequency total current ($Q_o$) flows via the flow impedance (3), while a second partial current ($Q_2$) flows via the mouthpiece into the respiratory tract of a test subject, characterized in that, in order to determine that particular second partial current ($Q_2$) of the impressed higher-frequency total current ($Q_o$), which flows via the mouthpiece (2) into the respiratory tract of the test subject, said apparatus further comprises: signal forming means (7–18) coupled with said pulse generator means (5, 6) for supplying a first signal in accordance with the higher frequency total current ($Q_o$) and coupled with said selective pressure measuring means (12) for supplying a second signal in accordance with the first partial current ($Q_1$), and a subtractor means (19) connected to said signal forming means for subtracting the second signal from the first signal to provide a third signal in accordance with the second partial current ($Q_2$) which flows via the mouthpiece, said signal forming means (7–18) comprising a phase tuning means (17, 18) connected to the subtractor means, and adjustable during a calibration operation carried out while the breathing tube (1) is sealed off at the mouthpiece (2) to bring the first signal and the second signal substantially into phase with one another.

2. Apparatus according to claim 1, characterized in said phase tuning means having at least one regulatable phase shifter means (18) for the purpose of equalizing the phase of the first signal according to the total current ($Q_o$) and the second signal representing the first partial current ($Q_1$) during the calibration operation.

3. Apparatus according to claim 2, characterized in said phase tuning means having an additional fixed phase shifter means (17) for introducing a phase shift according to the phase angle ($\phi_o$) associated with the known impedance value ($Z_o$), said additional fixed phase shifter means being interposed between the pressure measuring means (12) and an input of the subtracter means (19) for adjusting the phase of the second signal in conformity with the phase of the first partial current ($Q_1$).

4. Apparatus according to claim 1, characterized in that, for the determination of the phase ($\phi$) of the respiratory passageway impedance (Z), said apparatus further comprises: phase measurement means (28), means for connecting said phase measurement means in the signal path for the third signal representing the second partial current ($Q_2$) behind the subtractor means (19), on the one hand, and for connecting said phase measurement means for sensing the pressure signal (P) on the other hand; and during the calibration operation carried out while the breathing tube (1) is sealed off at the mouthpiece (2), for connecting the phase measurement means (28) in the signal path for the first signal representing the total current ($Q_o$) and in the signal path for the second signal representing the first partial current ($Q_1$), with the phase tuning means (17, 18) being adjustable to provide a null phase difference as sensed by said phase measurement means.

5. Apparatus according to claim 1, characterized in the signal forming means (7–18) comprising a first signal means (7, 8, 9, 14) coupled to said pulse generator means (5, 6) for producing the first signal in the form of a phase-synchronous sinusoidal signal synchronous with the impressed total current ($Q_o$).

6. Apparatus according to claim 5, characterized in the pulse generator means (5, 6) comprising an alternating flow pump (5) having a drive unit (6) connected to said first signal means (7, 8, 9, 14) for the purpose of producing the phase-synchronous sinusoidal signal synchronous with the impressed total current ($Q_o$).

7. Apparatus according to claim 6, characterized in the first signal means comprising a light barrier (7) coupled to the drive unit (6) for rotation therewith, an optical transmitter (8) and an optical receiver (9) having a path for light rays therebetween which path is periodically interrupted by the light barrier (7) rotating with the drive unit (6) of the pump (5) to produce a square wave signal; and a selective filter means (14) connected with said optical receiver for filtering out said phase-synchronous sinusoidal signal from the square wave signal.

8. Apparatus according to claim 1, 2, 3, 4, 5 or 6, characterized in that, in order to determine the magnitude of the respiratory passageway impedance (Z), said apparatus further comprising circuit means (21, 22) connected with said signal forming means (7–18) for receiving a signal responsive to the pressure signal (P) and for rectifying said averaging the received signal to provide a fourth signal according to the rectified and averaged pressure signal, and a divider means (24) connected with said subtracter means (19) and with said circuit means (21, 22) for supplying a quotient signal according to the quotient of the fourth signal and the third signal, and a calibration potentiometer (25) and a calibratable indicator (26) connected in series to the output of the divider means (24).

9. Apparatus according to claim 1, 2, 3, 4, 5 or 6, characterized in said apparatus further comprising indicator means (26, 29) having coupled switches (27, 30) actuatable respectively to measurement and calibration switching conditions, and operable in the measurement switching condition to connect the indicator means with the signal forming means to display measured parameters according to the respiratory passageway impedance, and operable in the calibration switching condition to connect the indicator means with the signal forming means to indicate when the phase tuning means (17, 18) is adjusted during the calibration operation to bring the first and second signals into phase with one another.

10. Apparatus according to claim 1, characterized in that, in order to directly determine the real component and the imaginary component of the respiratory passageway impedance (Z), said apparatus further comprises rectifier means (31) connected with said signal forming means for receiving a signal responsive to said pressure signal (P) and for rectifying the received signal to provide a rectified signal according to the rectified pressure signal, magnitude forming means (32, 37) connected with the subtractor means (19) for receiving a signal in accordance with the second partial current ($Q_2$) and for supplying a magnitude signal according to the magnitude of the second partial current ($Q_2$), a divider means (33) connected with said rectifier means (31) and with said magnitude forming means (32, 37) for supplying a quotient signal according to the quotient of the rectified pressure signal and the magnitude of the second partial current ($Q_2$) such that the quotient signal at the time of occurrence of a peak value of the second partial current ($Q_2$) corresponds to the real component of the respiratory passageway impedance (Z), and at the time of occurrence of a zero crossing of the second partial current ($Q_2$) corresponds to the magnitude of the imaginary component of the respiratory passageway impedance (Z).

11. Apparatus according to claim 10, characterized in that, in order to detect the magnitude of the second partial current ($Q_2$), said apparatus further comprises sample and hold means (37) functioning as part of said magnitude forming means (32, 37) and connected with said divider means (33) for supplying to said divider means (33) the magnitude signal according to the magnitude of the second partial current ($Q_2$), and peak value detector means (35, 36) connected with said subtracter means (19) and controlling said sample and hold means (37), and operable for generating sample pulses in response to the peak values of the second partial current ($Q_2$) for the purpose of actuating said sample and hold means (37).

12. Apparatus according to claim 11, characterized in the peak value detector means comprising differentiating means (35), and zero value detector means (36) connected to the differentiating means.

13. Apparatus according to claim 10, characterized in that, in order to detect the quotient signal at the time of a peak value of the second partial current ($Q_2$), said apparatus further comprises sample and hold means (38) connected with the output of said divider means (33) for detecting the magnitude of a signal in accordance with the quotient signal therefrom; and peak value detector means (35, 36) connected with said subtractor means (19) and controlling said sample and hold means (38), and operable for generating sample pulses in response to the peak values of the second partial current ($Q_2$) for the purpose of actuating said sample and hold means (38), thereby to provide an output in accordance with the real value of the respiratory passageway impedance (Z).

14. Apparatus according to claim 10, characterized in that, in order to detect the quotient signal at the time of a zero value of the second partial current ($Q_2$), said apparatus further comprises sample and hold means (41) connected with the output of said divider means (33) for detecting the magnitude of a signal in accordance with the quotient signal therefrom; and zero value detector means (40) connected with said subtractor means (19) and controlling said sample and hold means (41), and operable for generating sample pulses in response to zero crossings of the second partial current ($Q_2$) for the purpose of actuating said sample and hold means (41), thereby to provide an output in accordance with the magnitude of the imaginary component of the respiratory passageway impedance (Z).

15. Apparatus according to claim 14, characterized in that, in order to obtain a polarity determination of the imaginary component of the respiratory passageway impedance (Z), said apparatus further comprising an inverter means (45) connected with the output of the sample and hold means (41) for transmitting an output signal according to the magnitude of the imaginary component of the respiratory passageway impedance (Z) which is of opposite polarity, and selector means (44) responsive to the phase of the pressure signal relative to the phase of the third signal which is in accordance with the second partial current ($Q_2$) for controlling selective display of the output of the sample and hold means (41) and of the inverter means (45) according thereto.

16. Apparatus according to claim 15, characterized in that, in order to determine the phase of the pressure signal (P) relative to the phase of the second partial current ($Q_2$), said apparatus comprises further sample and hold means (42) having an input for receiving a signal according to said pressure signal (P) and having an output connected with said selector means (44), and said zero detector means (40) being responsive to a particular transition of the waveform of the second partial current ($Q_2$) to actuate said further sample and hold means (42), and said selector means (44) comprising a comparator means for comparing the output voltage from the sample and hold means (42) with ground potential.

* * * * *